(12) United States Patent
Brahm

(10) Patent No.: US 10,058,632 B1
(45) Date of Patent: Aug. 28, 2018

(54) NANOPARTICLE-CONTAINING PLACENTAL CONSTRUCTS AND METHODS OF USE

(71) Applicant: Brahm Holdings, LLC, Germantown, TN (US)

(72) Inventor: Timothy R. Brahm, Germantown, TN (US)

(73) Assignee: Brahm Holdings, LLC, Germantown, TN (US)

( * ) Notice: Subject to any disclaimer, the term of this patent is extended or adjusted under 35 U.S.C. 154(b) by 0 days.

(21) Appl. No.: 15/614,950

(22) Filed: Jun. 6, 2017

Related U.S. Application Data

(63) Continuation of application No. 14/988,841, filed on Jan. 6, 2016, now Pat. No. 9,694,109.

(60) Provisional application No. 62/100,204, filed on Jan. 6, 2015.

(51) Int. Cl.
*A61L 27/54* (2006.01)
*A61K 35/50* (2015.01)
*A61K 33/06* (2006.01)
*A61L 27/36* (2006.01)
*A61L 27/40* (2006.01)

(52) U.S. Cl.
CPC ........... *A61L 27/54* (2013.01); *A61K 33/06* (2013.01); *A61K 35/50* (2013.01); *A61L 27/3604* (2013.01); *A61L 27/40* (2013.01); *A61L 2430/02* (2013.01); *A61L 2430/34* (2013.01)

(58) Field of Classification Search
None
See application file for complete search history.

(56) References Cited

U.S. PATENT DOCUMENTS

| 7,871,646 B2 * | 1/2011 | Ghinelli | A61K 35/48 424/520 |
| 2007/0020336 A1 * | 1/2007 | Loftsson | A61K 9/0043 424/486 |
| 2014/0052247 A1 * | 2/2014 | Daniel | A61L 27/50 623/13.11 |

OTHER PUBLICATIONS

Liu (Seminars in Plastic Surgery 2005, 19(3):241-250).*
Hong et al. (Journal of Pharmacopuncture 2012;15(3):013-018).*

* cited by examiner

*Primary Examiner* — Robert A Wax
*Assistant Examiner* — Quanglong N Truong
(74) *Attorney, Agent, or Firm* — Brinks Gilson & Lione

(57) ABSTRACT

A placental construct is provided. The placental construct includes a therapeutically effective amount of human birth tissue material and a nanoparticle composition. Methods of treatment with the placental construct and a corresponding kit are also provided.

14 Claims, No Drawings

NANOPARTICLE-CONTAINING PLACENTAL CONSTRUCTS AND METHODS OF USE

CROSS-REFERENCE TO RELATED APPLICATIONS

This application is a continuation of U.S. application Ser. No. 14/988,841 filed Jan. 6, 2016, which claims priority to U.S. Provisional Application No. 62/100,204 filed Jan. 6, 2015, the entirety of each is incorporated herein by reference.

BACKGROUND OF THE INVENTION

Human placental tissue has been used in various surgical procedures, including skin transplantation and ocular surface disorders, for over a century. The tissue has been shown to provide good wound protection, prevent surgical adhesions, reduce pain, reduce wound dehydration, and provide anti-inflammatory and anti-microbial effects.

The placenta is a fetomaternal organ consisting of a placental globe, umbilical cord, associated membranes (chorionic membrane and amniotic membrane), other gelatins, fluids, cells and extracellular material. The chorionic membrane and the amniotic membrane are attached by loose connective tissue and make up the placental sac. The innermost membrane of the placental sac is the amniotic membrane, which comes into contact with the amniotic fluid that surrounds the fetus. The amniotic membrane is avascular and lined by simple columnar epithelium overlying a basal membrane. The chorionic membrane is the outermost layer of the sac and is heavily cellularized. The placental membranes have an abundant source of collagen that provides an extracellular matrix to act as a natural scaffold for cellular attachment in the body. Collagen provides a structural tissue matrix that facilitates, among other things, cell migration and proliferation in vivo.

While human placental tissue exhibits the aforementioned advantageous properties, there still remains a need for a placental construct that not only aids in the healing cascade but also is capable of providing antimicrobial, antiviral, antifungal, angiogenic, neurogenic, collagenic, and osteogenic properties or any combination thereof.

SUMMARY OF THE INVENTION

A placental construct is provided that includes a therapeutically effective amount of human birth tissue material and a nanoparticle composition. According to one embodiment, the birth tissue material includes one or more components of a human placental organ including the placental globe, the umbilical cord, the chorionic membrane, the amniotic membrane, and amniotic fluid. According to one embodiment, the placental construct is formulated as a flowable, injectable semi-solid, a single layer graft, or a multi-layer graft. According to one embodiment, the nanoparticle composition includes one or more elemental nanoparticles. Suitable elemental nanoparticles include, but are not limited to, silver, gold, magnesium, copper, aluminum, titanium, indium, cobalt, nickel, silicon, zirconium, samarium, lanthanum, and zinc. According to another embodiment, the nanoparticle composition includes one or more nanoparticles that are elemental ions. Suitable elemental ions include, but are not limited to, silver, gold, magnesium, copper, aluminum, titanium, indium, cobalt, nickel, silicon, zirconium, samarium, lanthanum, and zinc ions. The nanoparticle composition may include oxides of the elements provided herein (e.g., $TiO_2$). According to one embodiment, the nanoparticle composition may include one or more impurities including osmium, rhenium, rhodium, tin, platinum, lithium, sodium, silver, zinc, silicon, carbon, nitrogen, sulfur, iron, moldybdenum, rubidium, copper, and potassium. According to one embodiment, the nanoparticle composition is dispersed within the human birth tissue material, applied to an inside surface of the resulting placental construct, or applied to an outside surface of the construct. According to one embodiment, the placental construct exhibits antimicrobial, antiviral, antifungal, angiogenic, neurogenic, collagenic, and osteogenic properties or any combination thereof. According to one embodiment, the placental construct further comprises amniotic fluid, amniotic fluid components, or a combination thereof. According to one embodiment, the human birth tissue material is cellularized (i.e., not manipulated in any way to decellularize or remove cells or cellular components).

According to another aspect, a method of treating a skin condition or soft tissue defect of the skin is provided. The method includes the step of applying an effective amount of the placental construct to the skin condition or soft tissue defect of the skin. According to one embodiment, the skin condition is an ischemic wound, scar, traumatic wound, severe burn, or surgical wound. According to one embodiment, the skin condition is keratosis, melasma, pruritus, spider veins, lentigo, dermatitis, psoriasis, folliculitis, rosacea, impetigo, erysipelas, erythrasma, or eczema.

According to another aspect, a method of treating a bone defect is provided. The method includes the step of administering an effective amount of the placental construct to the bone defect. According to one embodiment, the placental construct aids in bone regeneration.

According to another aspect, a method of preventing or killing a pathological infection at a site on or within the body is provided. The method includes the step of administering an effective amount of the placental construct to the site. According to one embodiment, the placental construct includes a nanoparticle composition that includes magnesium ions.

According to another aspect, a kit is provided that includes a placental construct as provided herein. The kit may further include a set of instructions for use thereof.

DETAILED DESCRIPTION OF THE INVENTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As used herein, the term "nanoparticle" encompasses particles having one dimension that is less than about 100 nanometers in size.

As used herein, the term "nanoparticle composition" refers to any substance that contains at least one nanoparticle.

As used herein, "human birth tissue" encompasses one or more of the components of the placental organ including, but not limited to, the placental globe, the umbilical cord, the umbilical cord blood, the chorionic membrane, the amniotic membrane, the Wharton's jelly, other gelatins, cells, and extracellular material, and the amniotic fluid.

As used herein, "placental tissue components" encompasses one or more of the tissue components of the placental organ including, but not limited to, the placental globe, the umbilical cord, the umbilical cord blood, the chorionic membrane, the amniotic membrane, the Wharton's jelly and other gelatins, cells and extracellular material.

As used herein, the term "amnion" and "amniotic membrane" are used interchangeably.

As used herein, the term "cellularized" refers to a tissue that is not manipulated in any way to decellularize or remove cells or cellular components.

A placental construct is provided. The placental construct includes human birth tissue and at least one nanoparticle composition. The human birth tissue can be prepared according to the steps provided herein and combined with the nanoparticle composition to formulate a placental construct that exhibits antimicrobial, antiviral, antifungal, angiogenic, neurogenic, collagenic, osteogenic properties or any combination thereof. The placental construct is effective at preventing or killing pathological infection and promoting tissue and bone repair and regeneration.

According to one embodiment, the placental construct provided herein may be used to promote bone regeneration which is aided, in part, by the osteogenic properties of the nanoparticle composition. According to one embodiment, the placental construct provided herein exhibits increased mechanical strength for bone grafting purposes. According to one embodiment, the placental construct provided herein is capable of supporting osteogenic cell growth and differentiation. According to a particular embodiment, the placental construct provided herein aids in the sterilization and prevention of microbial growth at the site of use upon administration. According to a particular embodiment, the nanoparticle composition included in or on the placental construct aids in the sterilization of the construct. According to a particular embodiment, the nanoparticle composition included in or on the placental construct aids in preventing or reducing infection at a site where the placental construct may be placed on or within the body.

According to one embodiment, the placental construct as provided herein may be formulated in a variety of manners that are suitable for preventing or killing pathological infection and promoting tissue and bone repair and regeneration. According to one embodiment, the placental construct as provided herein may be formulated for any route of administration, including, but not limited to, oral (PO), intravenous (IV), intramuscular (IM), intra-arterial, intramedullary, intrathecal, subcutaneous (SQ), intraventricular, transdermal, interdermal, intradermal, rectal (PR), vaginal, intraperitoneal (IP), intragastric (IG), topical and/or transdermal (e.g., by lotions, creams, powders, ointments, liniments, gels, drops, etc.), mucosal, intranasal, buccal, enteral, vitreal, and/or sublingual administration. According to a particular embodiment, the placental construct is formulated as a flowable, injectable semi-solid. According to another embodiment, the placental construct as provided herein is formulated as a single or multi-layered graft. The placental construct as provided herein is suitable for application onto or into any part of the body.

To prepare the human birth tissue material for inclusion in a placental construct, placental tissue components and amniotic fluid are initially recovered from a seronegative, healthy human. Potential human birth tissue donors providing informed consent are pre-screened during an examination of pre-natal medical records and blood test results. A comprehensive medical history and behavior risk assessment is obtained from the donor prior to donation incorporating U.S. Public Health Service guidelines. Discussions with the physician(s) and/or the donor mother are conducted to identify circumstances that may lead to the exclusion of the donor or donated tissue. Additionally, a physical exam is performed on the donor to determine whether there is evidence of high risk behavior or infection and to determine the overall general health of the donor.

Infectious disease testing of donor blood specimens is performed for each tissue donor on a specimen collected at the time of donation or within seven days prior to or after donation. Advantageously, the methods that are used to screen for a communicable disease follow the regulations as set forth by the Federal Drug Administration and the American Association of Tissue Banks. Exemplary infectious disease testing includes, but is not limited to, antibodies to the human immunodeficiency virus, type 1 and type 2 (anti-HIV-1 and anti-HIV-2); nucleic acid test (NAT) for HIV-1; hepatitis B surface antigen (HBsAg); total antibodies to hepatitis B core antigen (anti-HBc—total, meaning IgG and IgM); antibodies to the hepatitis C virus (anti-HCV); NAT for HCV; antibodies to human T-lymphotropic virus type I and type II (anti-HTLV-I and anti-HTLV-II); and syphilis (a non-treponemal or treponemal-specific assay may be performed).

Human birth tissue is preferably recovered from a full-term Cesarean delivery of a newborn. Alternatively, human birth tissue is recovered from a full-term vaginal delivery of a newborn. The subsequent steps of preparing the human birth tissue material are performed in a controlled environment (i.e., certified biological safety cabinet, hood or clean room). Instruments, solutions, and supplies coming into contact with the human birth tissue material during processing are sterile. All surfaces coming in contact with the human birth tissue material intended for transplant are either sterile or draped using aseptic technique.

According to one embodiment, the placental tissue components include one or more components selected from the group consisting of amniotic membrane, chorionic membrane, Wharton's jelly, umbilical cord tissue, umbilical cord blood, placental globe, and other gelatins, other cells and extracellular matrix from placental tissue components. Other variations of the invention include, however, removing one or more of the placental globe, umbilical cord tissue, umbilical cord blood, chorionic membrane, amniotic membrane, or Wharton's jelly before further processing. Removal of one or more of the placental tissue components can be achieved via a sterile saline solution rinse, blunt dissection, scalpel, or a combination thereof, if necessary. According to one embodiment, the human birth tissue material is cellularized (i.e., not manipulated in any way to decellularize or remove cells or cellular components).

The retained placental tissue components can be placed in a sterile transport solution after aseptic recovery. The sterile transport solution is used to provide an advantageous medium to the natural function of tissue components prior to processing. Throughout the preparation of the human birth tissue material, various methods can be used to drive undifferentiated cells to differentiate into specialized cell types including, but not limited to, transport solutions, soaks, particular temperature ranges, and hyperbaric pressure.

The sterile transport solution preferably includes sodium chloride (NaCl) in a concentration range from typically about 10% to typically about 20% by weight. The sterile transport solution can also include one or more of Minimum Essential Medium, Dulbecco's Modified Eagle's Medium, Plasma Lyte-A, human albumin 25% solution, calcium-rich water, alkaline ionized water, or acidic ionized water.

Optionally, the placental tissue components may be soaked in a sterile saline solution for one or more soaks to remove all maternal components. In one embodiment, the sterile saline solution includes NaCl in a concentration range from typically about 10% to typically about 15% by weight.

Optionally, the placental tissue components can be cryopreserved according to methods commonly used in the art. The placental tissue components can be soaked in cryoprotectant prior to cryopreservation. In one embodiment, the cryoprotectant is one commonly used in the industry, such as, for example, dimethyl sulfoxide (DMSO). In a preferred embodiment, the cryoprotectant is an amnion control rate freeze solution comprising typically about 44% volume of Plasma Lyte-A, typically about 36% volume of human albumin 25% solution, and typically about 20% volume of dimethyl sulfoxide. In another embodiment, the cryoprotectant is a commercially available cryoprotectant such as Synth-a-Freeze® available from Invitrogen. Any cryoprotectant specific to the birth tissue material described herein may be used. In one embodiment, cryopreservation is achieved using a controlled rate freezer, resulting in a 1° C. rate from nucleation to −35° C. and a 10° C. per minute cooling rate to a −90° C. end temperature. However, any cryopreservation method commonly known in the art may be used.

The birth tissue material can be subjected to morselization. As used herein, "morselization" means to grind up to particle form. According to one embodiment, the morselized human birth tissue material renders the resulting placental construct flowable. According to one embodiment, the morselized human birth tissue material renders the resulting placental construct injectable. According to one embodiment, the morselized human birth tissue material renders the resulting placental construct able to conform to a particular area of treatment.

Tissue morselization may occur by any art-recognized method of tissue disruption, including, but not limited to: milling, blending, sonicating, homogenizing, micronizing, pulverizing, macerating, hand pressing, or a combination thereof. In one embodiment, the placental tissue components are subjected to cryogenic milling by methods commonly known in the art. In a preferred embodiment, the tissue is cryogenically milled in a CryoMill® (available from Retsch) for two cycles at a frequency 1/s of 25 Hz with a pre-cooling time of no more than about five minutes, a grinding time of no more than about two minutes, and an intermediate cooling time of no more than about five minutes. In another embodiment, a Freezer/Mill® available from SPEX SamplePrep, LLC may be used. After morselization, the milled human birth tissue material can be retained and preserved until combined with the carrier composition as described herein to formulate the final placental construct.

In one embodiment, the tissue may be morselized or otherwise rendered into fine particulates. Particles may be micron or submicron size ranges. In one embodiment, particle sizes may range from 1 micron to 100 microns. In another embodiment, particle sizes may range from 10 nm to 100 nm. Particles must be of sufficient size to allow diffusion through skin.

The resulting human birth tissue as provided herein may then be combined with a nanoparticle composition as provided herein to yield a placental construct. The nanoparticle composition may be dispersed within the human birth tissue material or applied to an inside surface or an outside surface of the construct (e.g., a graft). According to one embodiment, the nanoparticle composition is mixed or admixed with the human birth tissue as provided herein. According to one embodiment, the nanoparticle composition is mixed or admixed with the human birth tissue material as provided herein but no crosslinking is achieved between the nanoparticle composition and the human birth tissue material. According to one embodiment, the nanoparticle composition does not bond to or bond with the human birth tissue material as provided herein. The nanoparticle composition may include various components which may vary according to the end formulation and end use. The nanoparticle composition may include one or more nanoparticles or nanoparticle complexes that exhibit antimicrobial, antiviral, antifungal, angiogenic, neurogenic, collagenic, osteogenic properties or any combination thereof.

According to one embodiment, the nanoparticle composition includes one or more elemental nanoparticles. Suitable elemental nanoparticles include, but are not limited to, silver, gold, magnesium, copper, aluminum, titanium, indium, cobalt, nickel, silicon, zirconium, samarium, lanthanum, and zinc. According to another embodiment, the nanoparticle composition includes one or more nanoparticles that are elemental ions. Suitable elemental ions include, but are not limited to, silver, gold, magnesium, copper, aluminum, titanium, indium, cobalt, nickel, silicon, zirconium, samarium, lanthanum, and zinc ions. The nanoparticle composition may include oxides of the elements provided herein (e.g., $TiO_2$). According to one embodiment, the nanoparticle composition may further include a biocompatible drug, growth factor, and/or bioactive agent. Suitable bioactive agents include, but are not limited to, physiologically compatible minerals, growth factors, antibiotics, chemotherapeutic agents, antigen, antibodies, enzymes, vectors for gene delivery and hormones may also be added to the nanoparticle composition. According to one embodiment, the nanoparticle composition may further include a biocompatible polymer.

According to one embodiment, the nanoparticle composition may include one or more impurities (e.g., dopant, doping agent) that are introduced for the purpose of modifying the properties of the nanoparticle composition. Suitable impurities include osmium, rhenium, rhodium, tin, platinum, lithium, sodium, silver, zinc, silocon, carbon, nitrogen, sulfur, iron, moldybdenum, rubidium, copper, and potassium.

According to one embodiment, the nanoparticle composition may include one or more pharmaceutically acceptable excipients. Optionally, a suitable amount of amniotic fluid components may also be combined with the nanoparticle composition.

For topical applications, the placental construct may further include a carrier composition. The carrier composition can include any variety of components suitable for application to the human skin. According to one embodiment, the carrier composition includes one or more vitamins, minerals, proteins, fats, collagens (including collagen extracted from the placental globe), waxes, glycols and derivatives thereof, glyercols and derivatives thereof, oils (including essential oils), skin-abrading granules, fatty acids, cholesterols, alcohols, emollients, adsorbents, lubricants, moisturizing agents, emulsifying agents, thickening agents, humectants, surfactants, pharmaceutical ingredients, preservatives, antifungal agents, antioxidants, antimicrobial agents, structuring agents, dispersing agents, UV blocker and absorber ingredients (sunscreen), pH-adjusting components, sequestering or chelating agents, wetting agents and other components known in the art to be suitable for use in a placental construct.

The carrier composition can include other suitable components including, but not limited to, water, retinol, sorbitol, lanolin, beeswax, oleic acid, spermaceti, almond oil, egg oil, aloe, castor oil, tracacanth gum, clay, magnesia, talc, metal stearates, chalk, magnesium carbonate, zinc stearate, kaolin, glycerin, propylene glycol, polyethylene glycol, hyaluronic acid, chondroitin sulfate, elastin, polysaccharide, glycosaminoglycan, ascorbic acid, ascorbic acid derivatives, glucosamine ascorbate, arginine ascorbate, lysine or tyrosine ascorbate, gluthathione ascorbate, nicotinamide ascorbate, niacin ascorbate, allantoin ascorbate, creatine ascorbate, creatinine ascorbate, chondroitin ascorbate, chitosan ascorbate, DNA ascorbate, alpha hydroxyl acids, carnosine ascorbate, tocotrienol, rutin, quercetin, hesperedin, diosmin, mangiferin, mangostin, cyanidin, astaxanthin, lutein, lycopene, resveratrol, tetrahydrocurcumin, rosmarinic acid, hypericin, ellagic acid, chlorogenic acid, oleuropein, alpha-lipoic acid, niacinamide lipoate, gluthathione, andrographolide, carnosine, niacinamide, polyphenols, pycnogenol and mixtures thereof, benzophenones, benzotriazoles, homosalates, alkyl cinnamates, salicylates such as octyl salicylate, dibenzoylmethanes, anthranilates, methylbenzylidenes, octyl triazones, 2-phenylbenzimidazole-5-sulfonic acid, octocrylene, triazines, cinnamates, cyanoacrylates, dicyano ethylenes, etocrilene, drometrizole trisiloxane, bisethylhexyloxyphenol methoxyphenol triazine, drometrizole, dioctyl butamido triazone, terephthalylidene dicamphor sulfonic acid and para-aminobenzoates as well as ester derivatives thereof; antiacne agents such as salicylic acid; skin bronzing or tanning agent ingredients such as dihydroxyacetone, erytrulose, melanin; antioxidants such as vitamin C and derivatives thereof (e.g. ascorbyl acetate, ascorbyl phosphate and ascorbyl palmitate), vitamin A and derivatives thereof; folic acid and derivatives thereof; vitamin E and derivatives thereof such as tocopheryl acetate, flavons, or flavonoids, amino acids such as histidine, glycine, tyrosine, tryptophan, and derivatives thereof; carotenoids and carotenes; uric acid and derivatives thereof; citric acid, lactic acid, malic acid; stilbenes and derivatives thereof; and pomegranate extracts; vitamin K1 or K2, vitamin K1 oxide or vitamin K2 oxide, hormones, plant or botanical extracts, anti-inflammatory agents, concentrates of plant extracts, silicones, skin soothing ingredients, analgesics or anti-itch agents, skin penetration enhancers, solubilizers, alkaloids and processing aids; coloring agents including various dyes and pigments; perfumes or fragrances for the body; and other suitable components that do not interfere with the interaction between the birth tissue material and the various layers of the human skin.

The carrier composition is formulated in such a way that the combination of the birth tissue material and carrier composition are chemically compatible and do not form complexes which precipitate from the final placental construct. According to one embodiment, the carrier composition can be formulated as a cream, emulsion, lotion, gel, ointment, salve, butter, gel, putty, or balm. According to a preferred embodiment, the carrier composition is a cream.

The amount of human birth tissue material present in the placental construct can vary depending upon the location and purpose of use, the frequency of use, and the severity of the defect or condition to be treated. According to one embodiment, the placental construct includes a therapeutically effective amount of birth tissue material. According to one embodiment, the placental construct includes from typically about 0.1% to about 99.0% birth tissue material based on total placental construct weight. According to one embodiment, the placental construct includes from typically about 0.1% to about 99.0% of a nanoparticle composition as provided herein based on total placental construct weight.

Also provided herein is a kit that includes a placental construct as described herein. Such kits can include a package that is adapted to receive one or more containers, each of the container(s) including a placental construct as described herein. The kit is appropriately preserved up until and during shipment to a distributor or medical facility. The kit additionally includes at least one set of instructions for the end user including an explanation of how to apply, use, and maintain the placental construct.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

I claim:

1. A placental construct comprising:
    a therapeutically effective amount of human birth tissue material comprising at least one cellularized amniotic membrane, cellularized chorionic membrane, or a combination thereof; and
    a nanoparticle composition applied to an outside surface of the at least one cellularized amniotic membrane, cellularized chorionic membrane, or a combination thereof,
    wherein the placental construct is formulated as a single layer graft or multi-layer graft, and
    wherein the nanoparticle composition includes one or more elemental ion nanoparticles, one or more elemental nanoparticles, or one or more impurities.

2. The placental construct of claim 1, wherein the nanoparticle composition includes one or more elemental ion nanoparticles selected from the group consisting of silver, gold, magnesium, copper, aluminum, titanium, indium, cobalt, nickel, silicon, zirconium, samarium, lanthanum, and zinc.

3. The placental construct of claim 1, wherein the nanoparticle composition includes one or more elemental nanoparticles selected from the group consisting of silver, gold, magnesium, copper, aluminum, titanium, indium, cobalt, nickel, silicon, zirconium, samarium, lanthanum, and zinc.

4. The placental construct of claim 1, wherein the nanoparticle composition may include one or more impurities selected from the group consisting of osmium, rhenium, rhodium, tin, platinum, lithium, sodium, silver, zinc, silicon, carbon, nitrogen, sulfur, iron, moldybdenum, rubidium, copper, and potassium.

5. The placental construct of claim 1, wherein the placental construct exhibits antimicrobial, antiviral, antifungal, angiogenic, neurogenic, collagenic, osteogenic properties, or any combination thereof.

6. A method of treating a skin condition or soft tissue defect of the skin comprising:
    applying an effective amount of the construct of claim 1 to the skin condition or soft tissue defect of the skin.

7. The method of claim 6, wherein the skin condition is selected from the group consisting of an ischemic wound, scar, traumatic wound, severe burn, and surgical wound.

8. The method of claim 6, wherein the skin condition is selected from the group consisting of keratosis, melasma, pruritus, spider veins, lentigo, dermatitis, psoriasis, folliculitis, rosacea, impetigo, erysipelas, erythrasma, and eczema.

9. A method of treating a bone defect comprising
administering an effective amount of the placental construct of claim 1 to the bone defect.

10. The method of claim 9, wherein the placental construct aids in bone regeneration.

11. A method of preventing or killing a pathological infection at a site on or within the body comprising
administering an effective amount of the placental construct of claim 1 to the site.

12. The method of claim 11, wherein the nanoparticle composition comprises magnesium ions.

13. A kit comprising the placental construct of claim 1.

14. The kit of claim 13, further comprising instructions for use thereof.

* * * * *